United States Patent [19]

Schettler, Jr.

[11] Patent Number: 4,538,460
[45] Date of Patent: Sep. 3, 1985

[54] METHOD FOR DETERMINING PERMEABILITY

[75] Inventor: Paul D. Schettler, Jr., Huntingdon, Pa.

[73] Assignee: Columbia Gas System Service Corporation, Columbus, Ohio

[21] Appl. No.: 605,121

[22] Filed: Apr. 30, 1984

[51] Int. Cl.³ ............................................. G01N 15/08
[52] U.S. Cl. ...................................... 73/432 R; 436/5
[58] Field of Search ................ 73/38, 432 R, 432 PS, 73/432 Z; 436/5

[56] References Cited

U.S. PATENT DOCUMENTS 2,851,881  9/1958  Daniel et al. ............................ 436/5
3,262,319  7/1966  Orr et al. ......................... 73/432 PS

FOREIGN PATENT DOCUMENTS 0859864  8/1981  U.S.S.R. .................................. 73/38

Primary Examiner—S. Clement Swisher
Attorney, Agent, or Firm—Sidney W. Millard

[57] ABSTRACT

The permeability of samples, especially rock samples, is determined by immersing the sample in a dye solution to permit dye to diffuse into the sample, rinsing remaining dye solution from the surface and then either placing the rinsed sample in a leachback solution to permit dye to diffuse out into the leachback liquid or else simply allowing the dye to diffuse out onto the surface of the sample, thereby causing a coloration indicative of the permeability of the sample. The method can be practiced on slab samples or drill cuttings.

13 Claims, 1 Drawing Figure

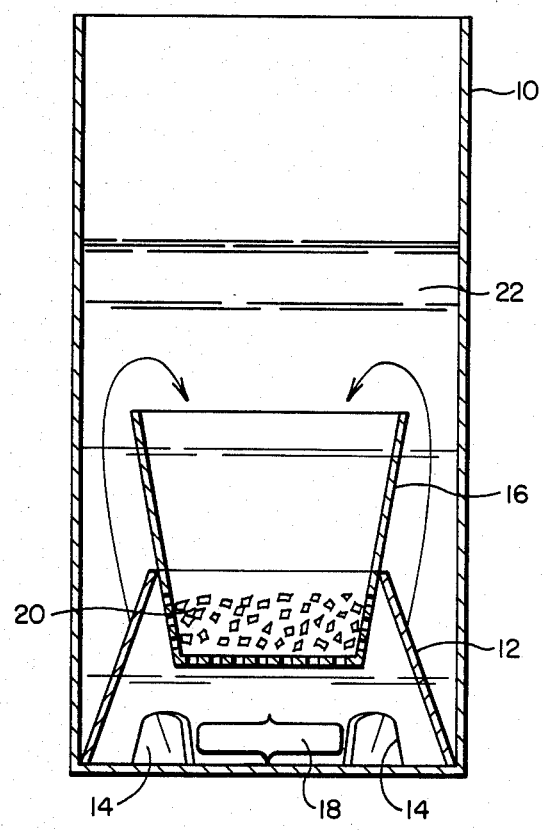

4,538,460

METHOD FOR DETERMINING PERMEABILITY

FIELD OF THE INVENTION

The invention relates to a method of determining permeability. This method is primarily intended for determining the permeability of rock samples.

BACKGROUND OF THE INVENTION

Those skilled in the field of gas well technology are aware that it is important to determine the permeability of the rock through which a well bore, drilled in search for gas, passes. Even if the well bore intersects a gas bearing stratum, significant levels of gas production can be obtained from the well only if the gas bearing stratum is sufficiently permeable to allow the gas to migrate readily to the well bore.

The permeability of a material is a measure of the rate that a fluid passes through the material under a pressure gradient. Prior art techniques for measuring permeability have been of two types. The first type, known as "plug methods", use a plug or slab of material for testing, establish a pressure gradient across this plug and measure the gas flow through the plug. Such methods suffer from the disadvantage that they require the preparation of a substantial plug of material, and such samples are not routinely available from most well drills, since the drills normally break up the rock being drilled into small drill cuttings or dust. Accordingly, it will normally be necessary to either interrupt the drilling process to produce a suitable core or else to cut cores laterally of the well bore after drilling has been completed; either approach obviously leads to undesirable delay. Plug methods also suffer from the serious disadvantage that the results are sensitive to the effects of fratures induced during sample preparation, and this sensitivity becomes enormous for low permeability samples. For example, measured permeabilities for shale may be as low as one picodarcy. A single 5 micron induced fracture 1 cm. long in a typical plug prepared from such shale will produce a permeability value in error by a factor of 1000. When preparing plugs from friable material such as shale, it is virtually impossible to avoid inducing fractures which will produce serious error in permeability measurements made by the plug technique.

The other major type of prior art permeability measuring methods is the so-called pressure pulse type. In pressure pulse methods, the pressure on one surface of a sample is varied with time, thereby creating internal pressure gradients within the sample, and the flow of fluid into or out of the sample produced by these internal pressure gradients is measured. Pressure pulse methods have the advantage that, since access to only one surface of the sample is required, the sample may be in the form of a slab, drill cuttings or dust (such as that produced by air rotary drills). In addition, pressure pulse methods are much less sensitive to the effects of induced fractures. However, as with plug methods, pressure pulse methods require relatively complicated methods and apparatus, and pressure pulse methods are also relatively slow. In practice, pressure pulse methods can only be conducted in the laboratory and are not suitable for routine use at the drill site.

It is also known to locate fractures in samples by allowing a dye to penetrate the sample, then spraying the sample with a white powder which shows where dye has entered fractures in the sample. Although such a dye penetrant method of locating fractures may give some qualitative indication of the permeability of a sample, it is incapable of being made sufficiently quantitative to be useful in determining permeability of rock strata during drilling of gas wells.

There is thus a need for a method for determining permeability of rock samples which permits permeability measurements to be made on samples in the forms of slabs, drill cuttings or similar small particles which is relatively simple and quick to carry out so that it can be routinely used at the well site to provide permeability measurements while drilling is in progress. This invention seeks to provide such a method.

SUMMARY OF THE INVENTION

The invention provides a method for determining the permeability of a sample in which the sample is contacted with a dye solution for a dyeing period sufficient to permit dye from the solution to diffuse into the sample. The sample is then separated from the dye solution and remaining dye solution rinsed from its surface. The rinsed sample is placed in a leachback liquid for a leachback period sufficient to permit dye from the rinsed sample to diffuse out into the leachback liquid and the amount of the dye which has so diffused from the sample into the leachback liquid is measured. (This method may hereinafter be referred to as the "leackback liquid" method of the invention.)

The term "dye" is used herein to mean a material which exhibits a characteristic pattern of absorption and/or emission of electromagnetic radiation within the range of wavelengths of electromagnetic radiation which can be handled by conventional optical devices such as lenses. Thus, the term "dye" as used herein includes not only materials which produce colors visible to the human eye but also materials which can only be detected using ultraviolet or infrared radiation, and also includes fluorescent dyes which produce characteristic fluorescense when illuminated with exciting light of an appropriate wavelength.

BRIEF DESCRIPTION OF THE DRAWING

The accompanying drawing shows schematically a vertical section through an apparatus used to carry out the instant leachback liquid method.

DETAILED DESCRIPTION OF THE INVENTION

The instant leachback liquid method measures permeability using a chemical potential gradient, namely dye concentration, rather than a pressure gradient, as in prior art pressure pulse methods. In this method, a sample which initially has a low (and normally zero) internal dye concentration is contacted with a dye solution having a high dye concentration, thereby causing dye to diffuse into the sample. The sample is then rinsed to remove any dye which is merely adhering to its surface, rather than which has diffused into the sample itself, and the rinsed, dye-containing sample is placed in a leachback liquid where the external dye concentration is lower than the internal dye concentration within the sample, so that dye diffuses out of the sample into the leachback liquid. It will be apparent to those skilled in the art that the amount of dye which diffuses into and thereafter out of the sample will be related to the permeability of the sample.

As already mentioned, the instant method is primarily intended for use in measuring the permeability of rock samples. However, I do not exclude the possibility that the instant method may be used for determining the permeability of other materials, for example, filter materials.

Because the instant method depends only upon diffusion of dye into and out of the sample, the sample may have a wide variety of physical forms. For example, the sample may be in the form of a solid slab, drill cuttings or dust (such as is produced by an air rotary drill). Where the sample is in the form of a solid slab it may be, for example, part of a drill core.

Although the sample used in the instant methods may be quite fine-grained, for best results the particles of the sample should not be small, and it is preferred that the sample be substantially free of particles smaller than about 50 U.S. mesh (about 30 microns). Indeed, in general it is preferred that the particles be not smaller than about 20–30 U.S. mesh (600–850 microns). There are two reasons for avoiding the use of particles which are too small. Firstly, in many rock samples much of the porosity of the bulk rock is due to thin microfractures and when the rock is broken down into small particles these microfractures become the faces of the smaller particles and hence cease to contribute to the measured permeability. Accordingly, if the particles are too small the measured permeability of the finely divided particles may not be representative of the permeability of the bulk material and it is of course the latter which is of importance in most applications. This decrease in permeability with particle size varies considerably from material to material being for example, much greater for sandstone than for shale. Secondly, when it is desired to use the instant leachback liquid method to determine relative permeabilities ("leachback values") which allow for differences in sample surface area, in concentration of dye solutions and in the various times used in the instant method (as described below) the equations used to calculate a "leachback constant" representative of permeability assume planar diffusion. The approximation caused by assuming planar diffusion is only reasonable if the "shell" of material into which the dye diffuses during contact of the sample with the dye solution is relatively thin compared to the diameter of the particle. Although the thickness of the shell will of course vary greatly with the permeability of the sample particles, if the sample particles were in contact with the dye solution for 15 minutes the diffusion shell may be several tenths of a millimeter thick. Such a thick shell may introduce substantial errors in the calculation of leachback values. Although the thickness of the shell can of course be decreased by decreasing the dying period, to calculate leachback values it is (as explained below) necessary to know the duration of the dyeing and other periods and if such periods are reduced too far, accurate timing of the periods becomes difficult.

For the foregoing reasons, it is preferred to carry out the instant leachback liquid method with particles of 8–10 U.S. mesh where possible, although in most cases particles of 10–20 U.S. mesh give no difficulty. Smaller particles should generally only be used with caution and with relatively short dyeing periods, and where possible the use of particles smaller than 50 U.S. mesh should almost always be avoided.

Because it is necessary for the calculation of leachback values that the surface area of the sample to be determined (see below), it will often be desirable to sieve the sample so that it only contains a narrow range of particle sizes. The preparation of appropriate slab samples will present no difficulty to those skilled in the art; for example, such slab samples may be cut from a core with a diamond saw. It has been found that slabs approximately $25 \times 25 \times 6$ mm. can conveniently be used in the instant leachback liquid method. Obviously, the use of a slab sample has the advantage that destruction of microfractures in preparation of the sample is minimized, but on the other hand slab samples are not routinely available during a drilling operation and must be especially prepared.

Since the instant method for determining permeability depends upon diffusion of the dye into and out of the sample, it is important that transport of the dye into the sample during the dyeing period occur only by diffusion and not by capillary action. Accordingly, it is desirable that the sample be substantially saturated with liquid before it is placed into the dye solution in order that dye will not be drawn into the sample by capillary action. Thus, prior to being contacted withh in the dye solution, the sample is preferably placed in a liquid and pre-soaked in order to substantially saturate the sample with liquid. Advantageously, the pre-soak liquid is identical to the dye solution except that, of course, the dye is omitted from the pre-soak liquid.

Certain types of rock, for example shales, exhibit complicated changess in leachback values with pre-soak time. For the first few days of soaking, shale leachback values drift towards high permeabilities, probably because the pre-soak liquid causes expansion of clay particles within the shale. Since the clay is a mixture of particle types, some particles expand more than others resulting in opening of pores and microfractures, thereby increasing the apparent permeability. Very long pre-soak times of the order of a few weeks reverse the earlier trend towards increased permeability, the apparent permeability decreasing with increasing soaking time. This decrease in permeability is probably due to breaking and plastic deformation of the clay particles which tends to plug pores within the shale. Although the variations in permeability with soaking time are not usually very great, to obtain truly comparable results from a plurality of samples it is advisable to establish a standard pre-soak time for all of the samples.

The sample (whether or not pre-soaked) is desirably contacted with the dye solution by immersing the sample in the dye solution. The dye used is very desirably one which is not sorbed by the sample since sorbing of a dye, for example rhodamine, by rock samples gives results which depend upon the degree of absorption as well as the pore structure of the sample and thus are not truly reflective of the permeability. Preferred dyes used in the instant methods are fluorescein dyes, especially fluorescein disodium salt, also known as Uranine. Uranine is normally not sorbed by minerals and fluorimetric methods for its detection in the leachback liquid are well-developed and comparatively easy to use. Conveniently, the Uranine is used at a concentration of about 0.1M in aqueous solution. To ensure that the fluorescein dye is present as the dianion throughout the instant methods (rather than as a variable mixture of dianion and monoanion, which would upset the assumptions on which the diffusion equations are based), the dye solution should be buffered to a pH of at least about 10. The optimum pH for Uranine buffer appears to be 10.3, and a bicarbonate/carbonate buffer adjusted to the appropriate pH with potassium hydroxide is a convenient buffer to use for this purpose. Preferably, the dye solution also contains potassium chloride, since it has been found that the presence of this salt inhibits the swelling and degrading interactions that can occur between certain clay minerals, if present in the sample, and an aqueous dye solution. It has been found that 2% by weight of potassium chloride in an aqueous dye solution gives good results.

Although, as already indicated, the dyeing period may need to be varied depending upon the permeability of the sample and the particle size therein, typical dyeing times in the instant processes are 50-600 seconds.

As already mentioned, when the dyeing period is over the sample is removed from contact with the dye solution (usually by lifting the sample out of the solution or by decanting the dye solution from the sample) and the sample is then rinsed to remove any dye solution remaining on its surface which, if carried into the leachback liquid, would give false results. Preferably, the rinsing liquid is identical to the dye solution except, of course, for the absence of dye. Conveniently, the rinsing is continued for a period of 30-360 seconds.

After the sample has been rinsed, in the instant leachback liquid method the sample is immersed in a leachback liquid, which is preferably identical to the dye solution except that the dye is omitted. Typical leachback periods used in this method are 70-840 seconds. Advantageously, two separate leachback periods are used with analysis of the leachback liquid being effected at the end of each leachback period; this provides an internal check on the accuracy of the procedure. Although in theory measurement of the amount of dye leached back into the leachback liquid could be effected while the leachback is still continuing, in practice it is normally necessary to separate the leachback liquid from the sample after a known leachback period and then to measure the amount of dye in the separated leachback liquid. Depending upon the nature of the dye used, determination of the amount of dye in the leachback liquid may be effected by colorimetric, fluorimetric or other techniques.

In order to minimize the percentage error in the leachback constant, it is desirable that the relative durations of the dyeing, rinse and leachback periods in the instant leachback liquid method be in the ratios of about 5:3:7. It is also desirable that, at least in the dyeing and leachback periods, the dye solution and leachback liquid be thoroughly stirred in order to ensure that the concentrations of dye immediately adjacent the sample be equal to the concentration in the bulk liquid. If, for example, thorough stirring is not maintained during the dyeing period, diffusion of dye into the sample will deplete the concentration of dye in the dye solution immediately adjacent the sample, thereby causing the effective concentration of dye "experienced" by the sample to be lower than the calculated dye concentration in the bulk solution, thus leading to error in the result.

The instant leachback liquid method may of course be used purely to determine the relative permeabilities of a series of samples. If a series of samples are seived or otherwise adjusted to the same particle size and are then subjected to the instant leachback liquid method using identical dyeing, rinse and leachback periods for each sample, the amounts of dye in the leachback liquids will be representative of the relative permeabilities of the samples. However, in most cases it will for obvious reasons be desirable to use the instant leachback liquid method to determine a "relative" permeability value which is independent of sample surface area, of concentration of the dye solution and of the dyeing, rinse and leachback periods used. It can be shown from conventional planar diffusion theory that a "leachback coefficient" independent of the sample surface area, concentration of the dye solution and dyeing, rinse and leachback periods may be defined from the equations:

$$L = (CV)/(2C_0AT)$$

Where:

$T = (t_0+t_1)^{\frac{1}{2}} - (t_0+t_2)^{\frac{1}{2}} + t_2^{\frac{1}{2}} - t_1^{\frac{1}{2}}$
$L$ = Leachback coefficient (liter/cm$^2$/sec$^{\frac{1}{2}}$)
$t_0$ = time that sample is removed from dye solution and placed in the rinse liquid (sec)
$t_1$ = time that sample is placed in leachback liquid (sec)
$t_2$ = time that sample is removed from leachback liquid (sec)
$C$ = concentration of dye in leachback liquid measured after $t_2$ and after dilution to volume V (moles/liter)
$V$ = final volume of leachback liquid (liters)
$C_0$ = concentration of initial dye solution (moles/liter)
$A$ = surface area of sample (cm$^2$)

In the above equations, the time zero is the time at which the sample is first contacted with the dye solution, $t_0$ is the time at which the sample is first contacted with the rinse liquid, $t_1$ is the time when the last drop of rinse liquid drips from the sample during transfer to the leachback liquid, and similarly $t_2$ is the time when the last drop of leachback liquid drips from the sample during its removal from the leachback liquid.

The determination of the surface area of the sample necessary for the above calculation may be determined by any of the conventional methods familiar to those skilled in the art. For example, where the sample is in slab form the area may be determined by direct measurement, the outline of the slab being traced on squared graph paper and the area determined by the usual square-counting technique. Alternatively, where the sample is in the form of small particles, the approximate surface area of a sample may be estimated from the formula $$A = 6w/sd$$

where:
w is the weight of the sample in grams
s is the specific gravity of the sample and
d is the mean particle diameter in centimeters.

Mean particle diameter may be estimated as the mean of the mesh sizes of the seives that caught and passed the sample. Alternatively, a known number (N) of particles may be weighed and d computed from the formula $$d = (w/sN)^{\frac{1}{3}}$$

Other techniques for estimating surface area will be apparent to those skilled in the art.

The presently preferred variant of the invention will now be described, though by way of illustration only, with reference to the accompanying drawing. As shown in the accompanying drawing, the apparatus used comprises a tall, cylindrical beaker 10, conveniently a long-style 250 ml beaker. A frusto-conical support member 12 formed from the top half of a plastic beaker is adhesively secured to the base of the beaker 10 with aquarium-type silicone sealer. The support member 12 has circulation holes cut therethrough adjacent the base of the beaker 10 to permit circulation of liquid within the beaker. A frusto-conical cup 16 formed from the lower part of a plastic beaker rests on the upper edge of the support member 12 so that the base of the cup 16 is spaced from the base of the beaker 10. The lower portion of cup 16 resting within support member 12 is perforated to allow liquid to circulate through a sample 20 which is retained within cup 16. (Alternatively, the bottom of the cup 16 may be replaced by a stainless steel or other mesh cemented to the cup using a water-resistant sealant, such as the silicone sealer previously mentioned.) A magnetic stirring bar 18 is located within the support member 12 beneath the cup 16. When the apparatus shown in the drawing is in use, it is placedd on a magnetic plate stirring device; such devices are familiar to those skilled in the art of chemistry. The stirring device causes bar 18 to rotate so as to force a solution 22 (which fills the beaker 10 to above the upper edge of the cup 16) downwardly through the sample 20 and upwardly outside the walls of the cup 16, thereby producing a continuous flow of solution 22 over the sample 22 and ensuring that the concentration of solution in contact with the sample 20 is the same as that in the bulk solution.

It should be noted that the cup 16 rests within the support member 12 only by virtue of its own weight and is freely removable therefrom. As explained in more detail below, the apparatus shown in the drawing is designed so that a single cup 16 containing a sample can be passed successively through a plurality of sets of apparatus in order to subject the sample to contact with pre-soak, dyeing, rinse and leachback liquids contained in the various sets of apparatus.

The presently preferred variant of the instant method uses a potassium bicarbonate/potassium carbonate/potassium hydroxide buffer containing potassium chloride as the pre-soak, rinse and leachback liquids, for the reasons already mentioned, and the same solution with the addition of uranine as the dye solution. A 1M buffer solution is made up by weighing out 20.0 grams of potassium chloride, 27.78 grams of potassium bicarbonate and 99.86 grams of potassium carbonate. All three salts are dissolved in appropriate volume of water (about 500 ml.) and made up to 1 liter. The pH of this 1M buffer solution is checked (the pH should be about 10.58). To prepare the final KCl/buffer solution, which contains 2% by weight of potassium chloride and is 0.01M in buffer, one volume of the 1M buffer solution is diluted with 99 volumes of 2% potassium chloride solution; this diluted buffer solution will have a pH of 10.3.

To prepare the dye solution, 37.515 g. (0.0997 moles) of uranine are dissolved in 800 ml. of the KCL/buffer solution, and the pH is raised to 10.3 by adding potassium hydroxide, one pellet at a time, while monitoring with a (previously standardized) pH meter. Finally, the solution is made up to one liter with more KCl/buffer solution and thoroughly mixed.

To carry out the determination of permeability, five separate sets of apparatus as shown in the drawing are prepared (without, of course, the cup 16 in position). Four of these sets of apparatus (to be used as pre-soak, rinse and two leachback solutions) are filled with the aforementioned 2% KCl/0.01M buffer solution, and the fifth apparatus is filled with the aforementioned uranine dye solution. 175 ml. of solution is used in each set of apparatus. A weight amount (10 to 15 g.) of sample are placed in a cup 16 and immersed for at least five minutes (and preferably at least thirty minutes) in the pre-soak KCl/buffer solution. The sample and cup are then removed from the pre-soak solution, the cup blotted dry from the bottom and the cup and sample placed in the dye solution. A stopwatch is started when the sample first contacts the dye solution.

As mentioned above, the appropriate dyeing period in the instant method depends upon the particle size in the sample. It has been found that two different sets of dyeing, rinse and leachback times cover most combinations of particle size and permeability encountered in practice with rock samples. The first time sequence (hereinafter referred to as the "long sequence") uses an overall time of 1320 seconds, while the second sequence (hereinafter referred to as the "short sequence") uses a total elapsed time of 440 seconds.

When using the long sequence, the cup and sample are removed from the dyeing solution at about 295 seconds, allowed to drain by gravity for approximately 5 seconds and then placed in a first KCl/buffer rinse solution at 300 seconds (equals $t_0$). When using the short sequence, the procedure is similar except that the times are adjusted so that $t_0=100$ seconds.

As already mentioned, we have found that it is highly desirable that three separate rinse solutions be used to secure accurate results. Accordingly, after about 15 seconds (315 seconds total elapsed time on long sequence, 115 seconds total elapsed time on short sequence) the sample is removed from the first rinse solution, rinsed with squirts from a wash bottle of the same solution and placed in a second, fresh rinse solution identical in composition to the first rinse solution. The first rinse solution can then be discarded and the beaker refilled with a fresh batch of the same solution to serve as the first leachback solution mentioned below. After about 465 seconds total elapsed time on the long sequence (145 seconds on the short sequence), the sample is removed from the second rinse solution, rinsed as before with the wash bottle, immersed in a third rinse solution (identical in composition to the first two) for approximately one second, removed from the third rinse solution and allowed to drain so that the last drop of rinse solution drains off at 480 seconds (equals $t_1$). On the short sequence, the procedure is similar except that $t_1$ is set at 160 seconds. Thereafter, the sample is immediately immersed in the first KCl/buffer leachback solution until a total lapsed time of 900 seconds (equals $t_2$), giving a first leachback period of 420 seconds on the long sequence. After removal from the first leachback solution, the sample is immediately immersed in the second leachback solution until a total elapsed time of 1320 seconds, so that the two leachbacks are conducted for 420 seconds each. On the short sequence, the leachbacks are each conducted for 140 seconds. At the end of each of the leachbacks, the sample is in fact removed approximately 5 seconds before the end of the leachback period and rinsed lightly with the KCl/buffer solution from a wash bottle, the washings being allowed to fall into the leachback liquid. The leachback solution plus washings is then diluted to 200 ml. in a volumetric flask and the concentration of uranine dye in the leachback solutions determined using a Turner Model 110 Fluorimeter which has previously been standardized using the technique described below. (Other types of fluorimeter can of course be used if desired.) The leachback constant may then be calculated, provided that the surface area of the sample has previously been determined in one of the ways suggested above.

The Turner Model 110 Fluorimeter is used with a primary (light source side) filter number 47B and a secondary (detector side) filter number 2A12. In addition, neutral density filters may be used as needed on the detector side, depending on concentration. Since the transmission characteristics of each filter are unique and the ranges on the range aperture only approximate, the filters should always be installed in the same orientation as when calibrated and kept clean to avoid data scatter.

The equations of fit for a fluorimeter are:

$$C = a_1 \ln(1 - a_2 F)$$

or $$F = a_2^{-1}[1 - \exp(C/a_1)]$$

F = Instrument reading
C = Concentration in moles/l and
$a_1$ and $a_2$ are empirically-determined constants, the former being independent of, and the latter dependent on, the range and neutral density filter being used.

From the above two equations, it will be seen that when F or C is small enough that only the first term within the logarithm need be taken into account:

$$C = a_1 a_2 F$$

In practice, the fluorimeter is operable over a uranine concentration range of $3.4 \times 10^{-9}$ to $6.0 \times 10^{-5}$M. The preferred variant of the instant leachback liquid process has been designed to produce uranine concentrations falling in the middle of this range, in which the effect of non-linearity is used to make about a 5% correction to the concentration.

To calibrate the fluorimeter, the dye solution described above is diluted with the KCl/buffer solution to produce standard solutions having uranine concentrations of $5.0 \times 10^{-6}$ to $10^{-4}$M. The fluorimeter is placed on the most concentrated range using both the 1% and 63% neutral density filters on the secondary side. A reading between 10 and 90 should be obtained on the fluorimeter; if the reading falls outside this range, the concentrations should be adjusted to give readings within the range.

The resultant data are fitted to the first equation above using a non-linear least squares routine to determine $a_1$ and $a_2$, plotting the data and the fitting equation to ascertain the quality of fit for the data. When a satisfactory fit is obtained, other fluorimeter ranges should be calibrated using 3-4 points per range keeping the value of $a_1$ calculated for the original range but using a linear least squares routine to determine $a_2$. Calibration should be effected for every (useable) combination of filters, the results in each case being checked by plotting.

To obtain accurate results it is important that the readings obtained from each solution do not vary with the particular sample holder employed and that the reading from any one sample holder does not change upon rotation of the sample holder. Also, the surfaces of the sample holders and the filters must be kept scrupulously clean and the instrument properly zeroed on each reading meaning both that firstly, with the door open, the instrument should be zeroed with adjustment on,off-/on switch (first) and that with the door closed the instrument should be zeroed using the KCl/buffer solution as a blank using the small knob next to the fluorescence reading dial with that dial set at 0 (second).

From the forthgoing description of the preferred variant of the invention, it will be seen that the instant leachback liquid method is sufficiently simple and quick to be operated on site to produce a rapid indication of well permeability from cuttings or other material produced while drilling is actually taking place, thereby enabling identification of high permeability zones which are the most likely gas producing zones in the well.

Because of the very great uncertainty in prior art plug type methods for measuring permeabilities of shales described above, it was not thought worthwhile to attempt to correlate leachback values measured by the instant leachback liquid method against such plug permeability values.

Measurements were also carried out on core samples obtained from wells drilled through gas-producing strata. The results show substantial increases in leachback values associated with the areas from which gas was produced.

Indications concerning the range of permeabilities over which leachback values obtained by the instant leachback liquid method can be expected to correlate with gas permeabilities were obtained from a study done with Selas glass porous plates. Such plates are made by partially fusing a carefully ground and seived glass and have pore sizes which vary over two orders of magnitude from plate to plate but porosities that remain almost constant. For such plates, the leachback values does not correlated well with permeability but remains constant as does the connected open porosity. The theoretical reason for this is that the flow profile of dye transport is constant across each pore, while for gas permeability more flow occurs in the center. Thus, for dye transport the total flow from a surface is simply the sum of all the cross-sectional areas of the pores whereas in gas permeability measurements large pores conduct gas out of proportion to their increased area.

Therefore, samples with low leachback values and hence low porosity will also have low gas permeability (as measured by specific degasibility). This semi-quantitative relationship does not extend to moderate and high leachback values because the instant leachback liquid method furnished is only pore volume information, not pore size. Nevertheless, rough comparisons can be made between leachback values and gas permeability values in the moderate to high ranges.

It will be apparent to those skilled in the art that numerous changes and improvements can be made in the preferred embodiment of the invention described above without departing from the scope of the invention. Accordingly, the foregoing description is to be construed in an illustrative and not in a limitative sense, the scope of the invention being defined solely by the appended claims.

I claim:

1. A method for determining the permeability of a sample, said method comprising:
    contacting said sample with a dye solution for a dyeing period sufficient to permit dye from said dye solution to diffuse into said sample;
    separating said sample from said dye solution and rinsing remaining dye solution from the surface of said sample; and placing said rinsed sample in a leachback liquid for a leachback period sufficient to permit said dye from said rinsed sample to diffuse into said leachback liquid; and measuring the amount of said dye which has diffused from said rinsed sample into said leachback liquid.

2. A method according to claim 1 wherein said sample is a rock sample.

3. A method according to claim 2 wherein said rock sample comprises at least part of a drill core.

4. A method according to claim 3 wherein said rock sample comprises drill cuttings.

5. A method according to claim 1 wherein said sample is substantially free of particles smaller than about 50 U.S. mesh.

6. A method according to claim 2 wherein said dye comprises a fluorescein dye.

7. A method according to claim 6 wherein said dye solution is buffered to a pH of at least about 10.

8. A method according to claim 6 wherein said dye solution further comprises potassium chloride.

9. A method according to claim 2 wherein said rinsing of said sample is effected using an aqueous rinse solution buffered to a pH of at least about 10.

10. A method according to claim 2 wherein said rinsing of said sample is effected using a rinse solution comprising potassium chloride.

11. A method according to claim 2 wherein said leachback liquid comprises an aqueous potassium chloride solution buffered to a pH of at least about 10.

12. A method according to claim 1 wherein said rinsing of said sample is continued for a rinse period and the relative durations of said dyeing, rinse and leachback periods are in the ratios of about 5:3:7.

13. A method according to claim 1 wherein, prior to contact with said dye solution, said sample is soaked in a liquid substantially free of said dye.

* * * * *